US008486244B2

(12) United States Patent
Cardosi et al.

(10) Patent No.: US 8,486,244 B2
(45) Date of Patent: Jul. 16, 2013

(54) TEST STRIP COMPRISING PATTERNED ELECTRODES

(75) Inventors: Marco F. Cardosi, Croy (GB); Leanne Mills, Croy (GB); Emma Vanessa Jayne Day, Duncanston (GB); Richard Michael Day, Duncanston (GB); Christopher Philip Leach, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 692 days.

(21) Appl. No.: 12/644,421

(22) Filed: Dec. 22, 2009
(Under 37 CFR 1.47)

(65) Prior Publication Data
US 2010/0206727 A1 Aug. 19, 2010

Related U.S. Application Data

(63) Continuation of application No. 12/305,358, filed on Oct. 5, 2007, now abandoned, which is a continuation of application No. PCT/GB2007/003790, filed on Oct. 5, 2007.

(60) Provisional application No. 60/850,212, filed on Oct. 5, 2006.

(51) Int. Cl.
*G01N 27/26* (2006.01)
*C12N 1/00* (2006.01)

(52) U.S. Cl.
USPC ............... 204/403.01; 204/403.04; 204/400

(58) Field of Classification Search
USPC ........................................ 204/400, 403.01
See application file for complete search history.

(56) References Cited

U.S. PATENT DOCUMENTS

| | | | |
|---|---|---|---|
| 5,708,247 A | 1/1998 | McAleer et al. | |
| 6,046,051 A | 4/2000 | Jina | |
| 6,179,979 B1 | 1/2001 | Hodges et al. | |
| 6,241,862 B1 | 6/2001 | McAleer et al. | |
| 6,448,794 B1 | 9/2002 | Cheng et al. | |
| 7,943,022 B2 * | 5/2011 | Teodorczyk et al. | 204/403.11 |
| 2003/0217918 A1 | 11/2003 | Davies et al. | |
| 2005/0096409 A1 | 5/2005 | Davies et al. | |
| 2005/0098434 A1 * | 5/2005 | Gundel et al. | 204/403.02 |
| 2007/0040567 A1 * | 2/2007 | Popovich et al. | 324/765 |

FOREIGN PATENT DOCUMENTS

| | | |
|---|---|---|
| EP | 1152239 A1 | 5/2001 |
| WO | WO 99/13099 A1 | 3/1999 |
| WO | WO 01/25775 A1 | 4/2001 |
| WO | WO 01/67099 A1 | 9/2001 |
| WO | WO 01/73124 A3 | 10/2001 |

(Continued)

OTHER PUBLICATIONS

International Search Report, International patent application No. PCT/GB2007/003790, dated Jan. 25, 2008, European Patent Office, Rijswijk, Netherlands, 4 pages.

(Continued)

*Primary Examiner* — Luan Van
*Assistant Examiner* — Steven Rosenwald

(57) ABSTRACT

Described herein is an electrochemical enzymatic analyte test strip and method for making the test strip. The test strip utilizes isolated conductive areas inside the electrodes to define electrode whiskers. The method utilizes laser ablation to define electrode patterns.

4 Claims, 6 Drawing Sheets

FOREIGN PATENT DOCUMENTS

| | | |
|---|---|---|
| WO | WO 02/00918 A3 | 1/2002 |
| WO | WO 2004/039600 A2 | 5/2004 |
| WO | WO 2004/039897 A2 | 5/2004 |
| WO | WO 2004/040005 A1 | 5/2004 |
| WO | WO 2004/040285 A1 | 5/2004 |
| WO | WO 2004/040287 A1 | 5/2004 |
| WO | WO 2004/040290 A1 | 5/2004 |
| WO | WO 2004/040948 A1 | 5/2004 |
| WO | WO 2005/047528 A1 | 5/2005 |
| WO | WO 2006/072089 A | 7/2006 |

OTHER PUBLICATIONS

Nadeem H. Rizvi, et al. "*An Excimer Laser Micromachining System for the Production of BioParticle Electromanipulation Devices*", Exitech Ltd., Hanborough Park, Oxford and Institute of Molecular and Biomolecular Electronics, University of Wales, Bangor, SPIE vol. 3224 (1997).

Erol C. Harvey et al., "*Fabrication Techniques and Their Applications to Produce Novel Micromachined Structures and Devices Using Excimer Laser Projection*" by, Exitech Ltd., Hanborough Park, Long Hanborough, Oxford, UK, SPIE vol. 3223, 1997.

Nadeem H. Rizvi, et al., "*Direct Manufacture of Miniature Bio-Particle Electro-Manipulator Devices Using Excimer Laser Mask Projection Techniques*", Exitech Ltd., and University of Wales, UK (Aug. 12, 1998).

Japanese abstract, Japanese publication No. 05-072172, publication date Mar. 23, 1993.

Japanese abstract, Japanese publication No. 11-304748, publication date Nov. 5, 1999.

\* cited by examiner

TEST STRIP COMPRISING PATTERNED ELECTRODES

PRIORITY

This application is a continuation and claims the benefit of priority under 35 USC §§119 and 120 to U.S. patent application Ser. No. 12/306,358, International Application filing date Oct. 5, 2007, which claims priority from International Application Number PCT/GB2007/003790, filed Oct. 5, 2007, which claims priority from Provisional Application Ser. No. 60/850,212, filed on Oct. 5, 2006, in which all applications are incorporated by reference in their entirety herein.

BACKGROUND

Various glucose test strips have been described in the patent literature, such as, for example, JP5-72172 (Mar. 23, 1993; JP11-304748 (May 11, 1999); WO 01/25775; WO99/13099; EP1152239A1; WO02/00918A3; and WO2005/047528. One example of such test strips include electrochemical glucose test strips, such as those used in the OneTouch® Ultra® whole blood testing kit, which is available from LifeScan, Inc., are designed to measure the concentration of glucose in a blood sample from patients with diabetes. The measurement of glucose is based upon the specific oxidation of glucose by the enzyme glucose oxidase (GO). The reactions which may occur in a glucose test strip are summarized below in Equations 1 and 2.

Glucose+$GO_{(ox)}$→Gluconic Acid+$GO_{(red)}$    Eq. 1

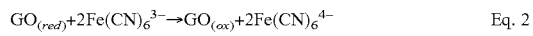

$GO_{(red)}$+2Fe(CN)$_6^{3-}$→$GO_{(ox)}$+2Fe(CN)$_6^{4-}$    Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state which is denoted as $GO_{(red)}$ (i.e., "reduced enzyme"). Next, the reduced enzyme $GO_{(red)}$ re-oxidized back to $GO_{(ox)}$ by reaction with Fe(CN)$_6^{3-}$ (referred to as either the oxidized mediator or ferricyanide) as illustrated in Equation 2. During the re-generation of $GO_{(red)}$ back to its oxidized state $GO_{(ox)}$, Fe(CN)$_6^{3-}$ is reduced to Fe(CN)$_6^{4-}$ (referred to as either reduced mediator or ferrocyanide).

When the reactions set forth above are conducted with a test voltage applied between two electrodes, a test current may be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose may, therefore, be referred to as a glucose current.

Because it can be very important to know the concentration of glucose in blood, particularly in people with diabetes, test meters have been developed using the principals set forth above to enable the average person to sample and test their blood for determining their glucose concentration at any given time. The glucose current generated is detected by the test meter and converted into a glucose concentration reading using an algorithm that relates the test current to a glucose concentration via a simple mathematical formula. In general, the test meters work in conjunction with a disposable test strip that includes a sample receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample receiving chamber, thus starting the chemical reaction set forth above.

In electrochemical terms, the function of the meter is two fold. Firstly, it provides a polarizing voltage (approximately 400 mV in the case of OneTouch® Ultra®) that polarizes the electrical interface and allows current flow at the carbon working electrode surface. Secondly, it measures the current that flows in the external circuit between the anode (working electrode) and the cathode (reference electrode). The test meter may, therefore be considered to be a simple electrochemical system that operates in a two-electrode mode although, in practice, third and, even fourth electrodes may be used to facilitate the measurement of glucose and/or perform other functions in the test meter.

As previously described, the amount of reduced mediator is measured at the working electrode through an oxidation current. The magnitude of the oxidation current is directly proportional to the working electrode surface area. Thus, in order to measure a glucose concentration in a precise and accurate manner, the working electrode area for a test strip must be reproducible and amenable to a robust manufacturing process. The ability to manufacture test strips with reproducible electrode areas becomes more difficult as the size of the working electrode area decreases. Because there is a market driven desire to reduce the volume of blood required to sufficiently fill a test strip, there is a need to manufacture test strips having a smaller working electrode area with high precision.

Test strips have often used an insulation layer to expose a pre-defined portion of the conductive layer, where the exposed portion is the effective working electrode area. Here, the effective working electrode area may be the area of the conductive layer capable of oxidizing a reduced mediator. The insulation layer may use an aperture or cutout to expose a portion of the conductive layer. One of the limitations of using an insulation layer may be that the aperture or cutout may not be sufficiently straight. Non-idealities of a straight edge may not significantly affect the working electrode area definition when the area is sufficiently large, but such non-idealities may become more of an issue as the working electrode area becomes smaller. As such, there is great interest in developing new methods for making test strips having a reproducible working electrode area that are robust and relatively inexpensive to implement.

SUMMARY OF INVENTION

In one embodiment, an analyte test strip is provided that includes a generally planar substrate, a first electrode track, and a first electrode. The generally planar substrate extends from a first end to a second end. The first electrode track extends between the first and second end of the substrate. The first electrode is located proximate the first end of the generally planar substrate and includes a first electroactive area disposed on the substrate proximate the first end. The first electroactive area includes a single continuous surface area of conductive material and a reagent disposed thereon with two spaced-apart first whisker tracks contiguous to both the first electroactive area and one end of the first electrode track.

In another embodiment, a method of making an analyte test strip is provided. The method can be achieved by: forming a layer of conductive material on a substrate; and removing selective portions of the conductive material to define a plurality of electrodes with each of the electrodes having two spaced-apart island of conductive material located in the electrode and electrically isolated from each of the electrodes; and depositing reagent over an area contiguous to the two spaced-apart islands to define an electroactive area of each electrode.

In one embodiment, the two whisker tracks and the two whisker electrodes may have an approximately rectangular shape. The two whisker tracks and the two whisker electrodes may each have a whisker width ranging from about 1 micron to about 20 microns.

In one embodiment, the conductive layer may be a sputtered gold film or a screen-printed carbon ink. The sputtered gold film may have a thickness ranging from about 20 nanometers to about 80 nanometers. In an alternative embodiment, the conductive layer may be sputtered gold that is insulatively etched using a photolithographic process.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF ILLUSTRATIVE EMBODIMENTS OF THE INVENTION

The present invention is directed to a method of making electrochemical test strips with reproducible electrode areas. In an embodiment of this invention, the process of laser ablation may be used to substantially define the electroactive portion of the working electrode. Further, an insulating pattern may be etched onto a conductive layer such that variations in an adhesive layer's alignment does not cause variations in the electroactive portion of the working electrode. The following sections will describe various embodiments of a test strip a method suitable for testing the test strip, and a method for making test strip embodiments of the present invention.

Figure 1A:
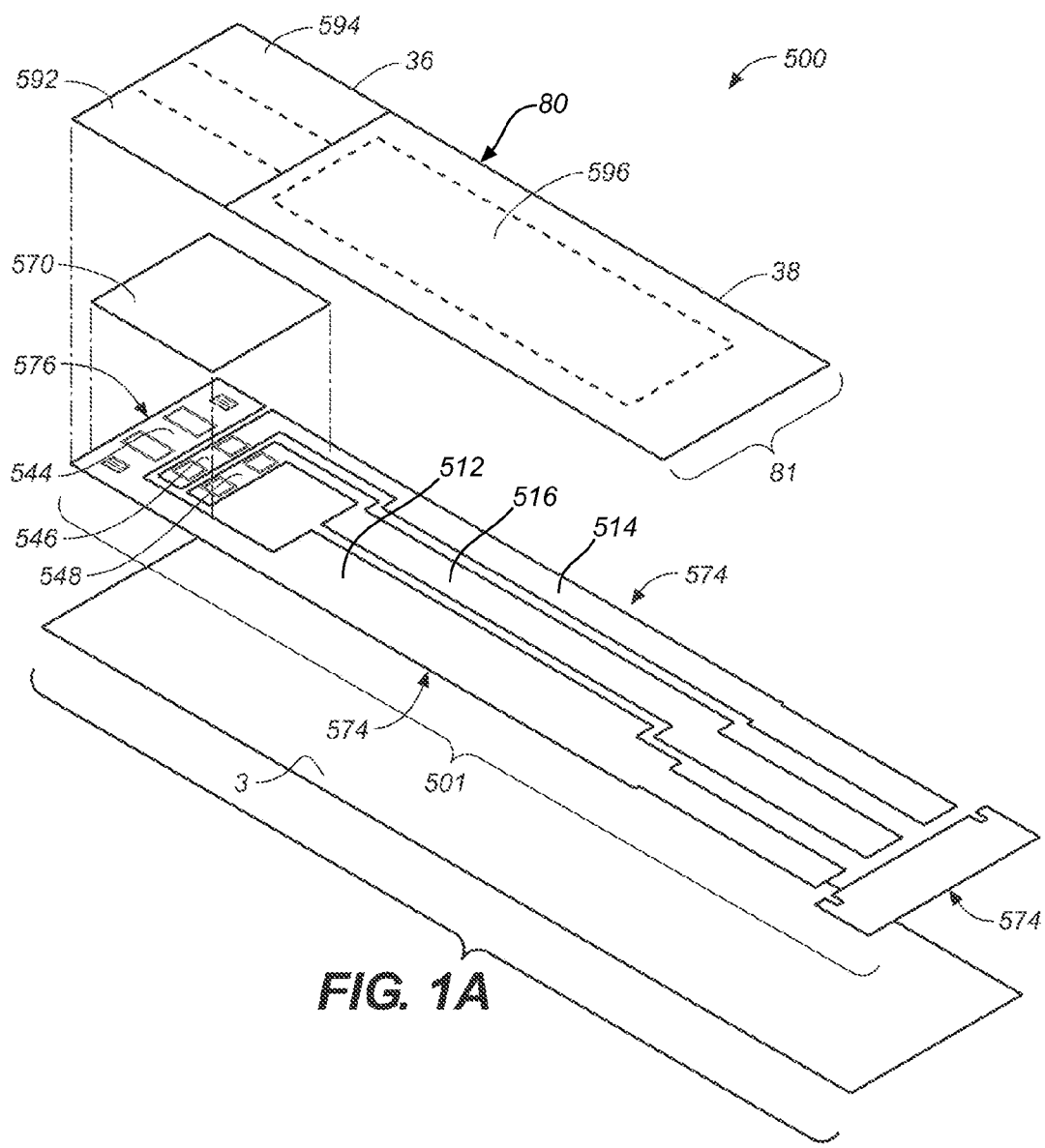
FIG. 1A illustrates a top exploded perspective view of an unassembled test strip which is an embodiment of the present invention.
Figure 2:
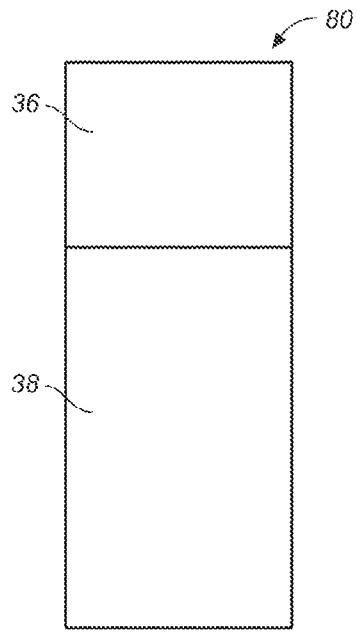
FIG. 2 illustrates a bottom plan view of a top tape which includes the top layer and an adhesive layer of FIG. 1A.
Figure 3:
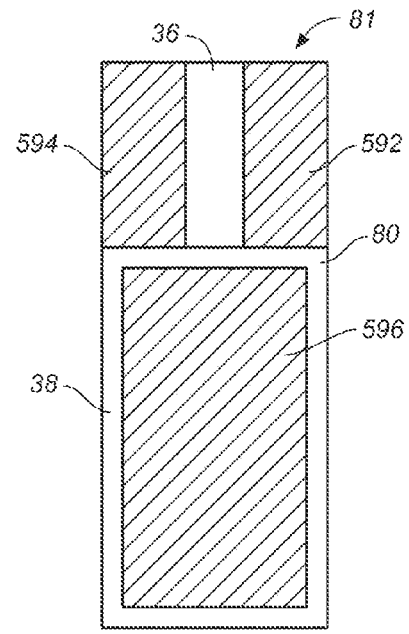
FIG. 3 illustrates a bottom plan view of a top layer which is one of the layers used for assembling the test strip of FIG. 1A.

FIG. 1A illustrates an embodiment having a top exploded perspective view of an unassembled test strip 500. Test strip 500 includes a conductive layer 501 having conductive tracks 512, 514, and 516 extending between the proximal end 574 and distal end 576 of the test strip 500, a reagent layer 570, and a top tape 81. Test strip 500 has a distal portion 576, a proximal portion 578, and two sides 574. FIG. 2 illustrates a bottom plan view of a top layer 80, which is one of the layers used for assembling test strip 500. Top layer 80 includes a clear portion 36 and an opaque portion 38. FIG. 3 illustrates a bottom plan view of top tape 81 which includes a top layer 80 having disposed thereupon a first adhesive pad 592, a second adhesive pad 594, and a third adhesive pad 596. It should be noted that test strip 500 does not include an insulation layer as in the known test strip, and thus, test strip 500 has the advantage of eliminating the step of printing an insulation layer for substantially defining the electroactive area for a first working electrode 546, a second working electrode 548, and a reference electrode 544.

The test strip 500 is provided with the reagent layer 570 having an enzyme ink. The enzyme ink may contain a filler having both hydrophobic and hydrophilic domains. Such filler may be disposed onto the working electrode using a screen-printing process. An example of a filler may be a silica such as, for example, Cab-o-Sil TS 610 which is commercially available from Cabot Inc., Boston, Mass. Typically, a screen may be in the form of a rectangular frame, which secures a plurality of interwoven threads. The plurality of interwoven threads form a plurality of open rectangular spaces for allowing enzyme ink to pass therethrough. The density and the size of the open spaces influence the amount of enzyme ink, which becomes deposited, on the conductive layer. Characteristics of the interwoven threads that influence the deposition of the enzyme ink are thread spacing and thread diameter. The thread spacing may range from about 90 threads per centimeter to about 120 threads per centimeter. The thread diameter may range from about 30 microns to about 50 microns. More specifically, in an embodiment, a screen suitable for screen-printing an enzyme ink having ruthenium hexamine and glucose oxidase may have a thread spacing of about 120 threads per centimeter and a thread diameter of about 34 microns.

Referring to FIG. 1A, a top tape 81 is provided for the test strip. The term top tape 81 refers to a combination of a top layer 80 (FIG. 2) of preferably a polyester material and spacer pads 592, 594, and 596 together, as illustrated in FIGS. 1A and 3. Top tape 81 may be assembled by a laminating process and stored in a roll format. FIG. 3 illustrates a bottom plan view of top tape 81 having a top layer with adhesive spacer pads 592, 594 and 596.

Figure 1B:
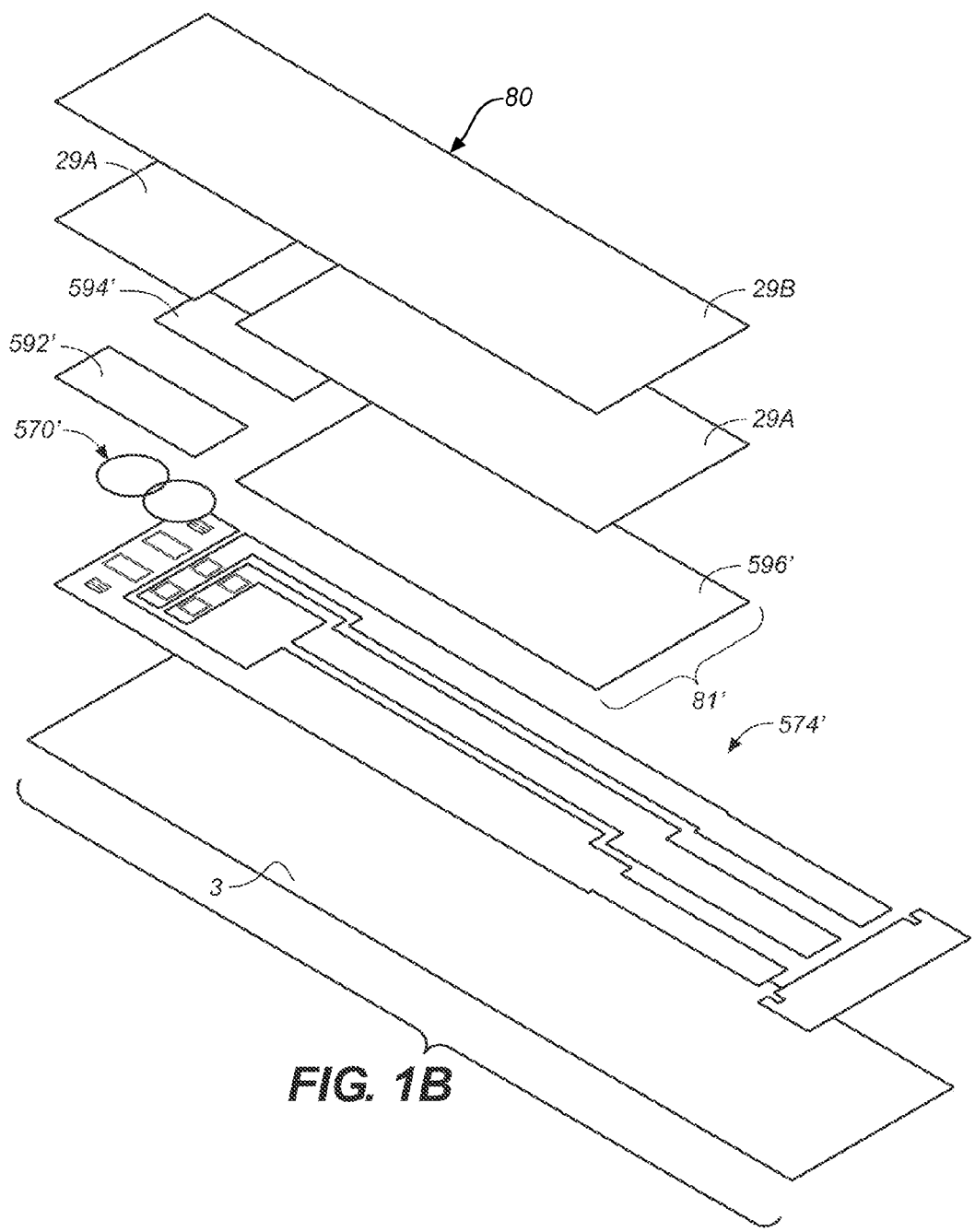
FIG. 1B illustrates an exploded perspective view of another embodiment of the test strip.

In another embodiment, illustrated as test strip 500' in FIG. 1B, an electrode pattern 574' is formed on substrate 3 with a reagent layer 570' disposed on the electrodes. A spacer 81' is provided which includes first adhesive spacer pad 592', second adhesive spacer pad 594', and third adhesive spacer pad 596'. Spacer 81' is disposed on a portion of insulation layer 16, conductive layer 50, and substrate 3. Preferably, spacer 81' can be made from double-sided adhesive polyester material. A hydrophilic film 29A (Mitsubishi) can be attached to the spacer 81' with a top tape 29B being attached to the hydrophilic film 29A via a medical grade pressure sensitive adhesive. A hydrophilic antifog coating in the form of a surfactant can be provided between the hydrophilic film and the spacer. In the preferred embodiment, the adhesives on both sides of the spacer pad, antifog coating, hydrophilic film, adhesive and top tape are provided as an integrated component in the form of a single laminate. It is worth noting that the test strip 500' of FIG. 1B utilizes an additional component in the form of a hydrophilic film as compared to the embodiment of FIG. 1A.

Embodiments of the test strip described herein may be manufactured using a process of laser ablation for improving the accuracy and precision of the electroactive area of the first and second working electrode such as described in the known literature, including, for example: "*An Excimer Laser Micromachining System for the Production of BioParticle Electromanipulation Devices*" by Nadeem H. Rizvi et al., Exitech Ltd., Hanborough Park, Oxford and Institute of Molecular and Biomolecular Electronics, University of Wales, Bangor, SPIE Vol. 3224 (1997); "*Fabrication Techniques and Their Applications to Produce Novel Micromachined Structures and Devices Using Excimer Laser Projection*" by Erol C. Harvey et al., Exitech Ltd., Hanborough Park, Long Hanborough, Oxford, UK, SPIE Vol. 3223, 1997; and "*Direct Manufacture of Miniature Bio-Particle Electro-Manipulator Devices Using Excimer Laser Mask Projection Techniques*" by Nadeem H. Rizvi et al., Exitech Ltd., and University of Wales, UK (Aug. 12, 1998). The process of laser ablation on a conductive layer allows the edge definition of the electrode area to be better controlled than with other processes such as screen-printing such as, for example, the screen-printing process as described in U.S. Pre-Grant Publication No. US20050096409A1 and published International Application No.'s WO2004040948A1, WO2004040290A1, WO2004040287A1, WO2004040285A2, WO2004040005A1, WO2004039897A2, and WO2004039600A2. In an alternative embodiment, an ink jetting process may be used to deposit the reagent layer, which is described in U.S. Pat. No. 6,179,979. In addition, the process of laser ablation may be used to substantially define the electrode area without the need of an insulation layer.

Figure 5:
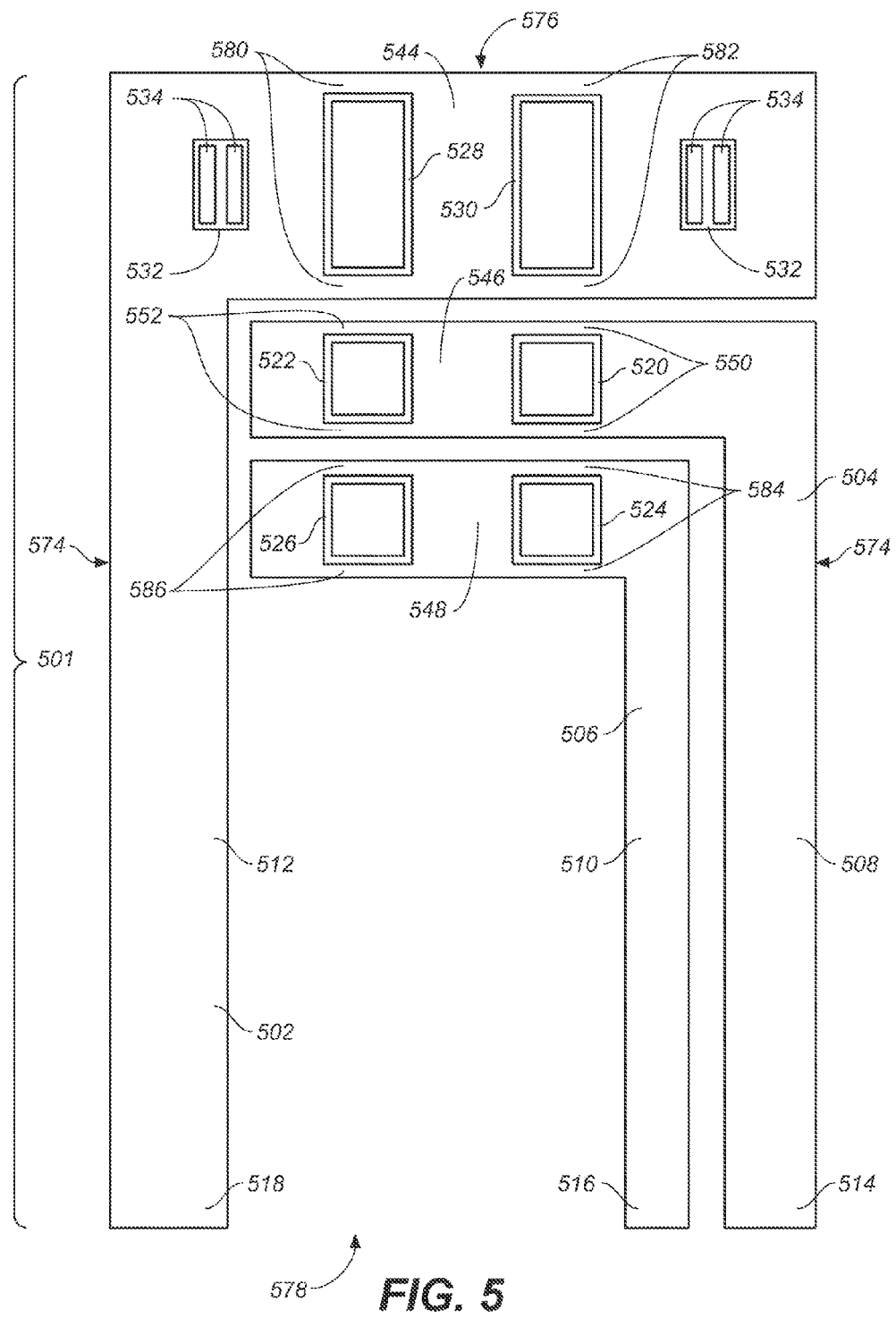
FIG. 5 is a simplified top view of a conductive layer having a laser ablated pattern for use in the test strip embodiment of this invention as shown in FIG. 1A.

FIG. 5 is a simplified top view of a conductive layer 501 (usable with either embodiments of FIG. 1A or FIG. 1B) having a laser-ablated pattern for use in a test strip 500. For test strip 500, a conductive layer 501 may be disposed on a suitable substrate such as, for example, polyester or polyethylene terephthalate (PET). For example, conductive layer 501 may be formed by sputtering a conductive material onto the substrate. Alternatively, conductive layer 501 may be formed by screen printing an unpatterned conductive carbon ink onto the entire substrate. Conductive layer 501 may then be insulatively etched into a first zone 502, a second zone 504, and an optional third zone 506, as illustrated in FIG. 5, using the process of laser ablation. The insulative etching process causes first zone 502, second zone 504, and third zone 506 to be electrically isolated with respect to each other. Conductive layer 501 may be gold, palladium, carbon, or other inert metal that can oxidize a reduced mediator in a quantitative manner. For a sputtered gold film, the gold may have a thickness ranging from about 10 nanometers to about 80 nanometers, and preferably about 15 nanometers or about 35 nanometers. The process of laser ablation may be performed with an Excimer laser which is commercially available from Tamarack Scientific Co., Inc. (220 Klug Circle, Corona, Calif., U.S.A.).

FIG. 5 shows that first zone 502 includes a reference pad 518, a reference electrode track 512, two whisker tracks 580, a reference electrode 544, two whisker electrodes 582, primary registration marks 532, secondary registration marks 534, a first polygon 528, and a second polygon 530. Reference pad 518 is located at proximal portion 578 and is adapted to connect to a test meter. There is an electrically continuous pathway that runs through the following elements, which are reference pad 518, reference electrode track 512, the two whisker tracks 580, reference electrode 544, and the two whisker electrodes 582. The two whisker tracks 580 each form an electrically continuous pathway, in parallel, between reference electrode 544 and reference electrode track 512. It is an advantage of this invention in that by having the two whisker tracks 580, electrical continuity can be maintained if a scratch or other insulating damage occurs at one of the two whisker tracks 580.

Figure 6:
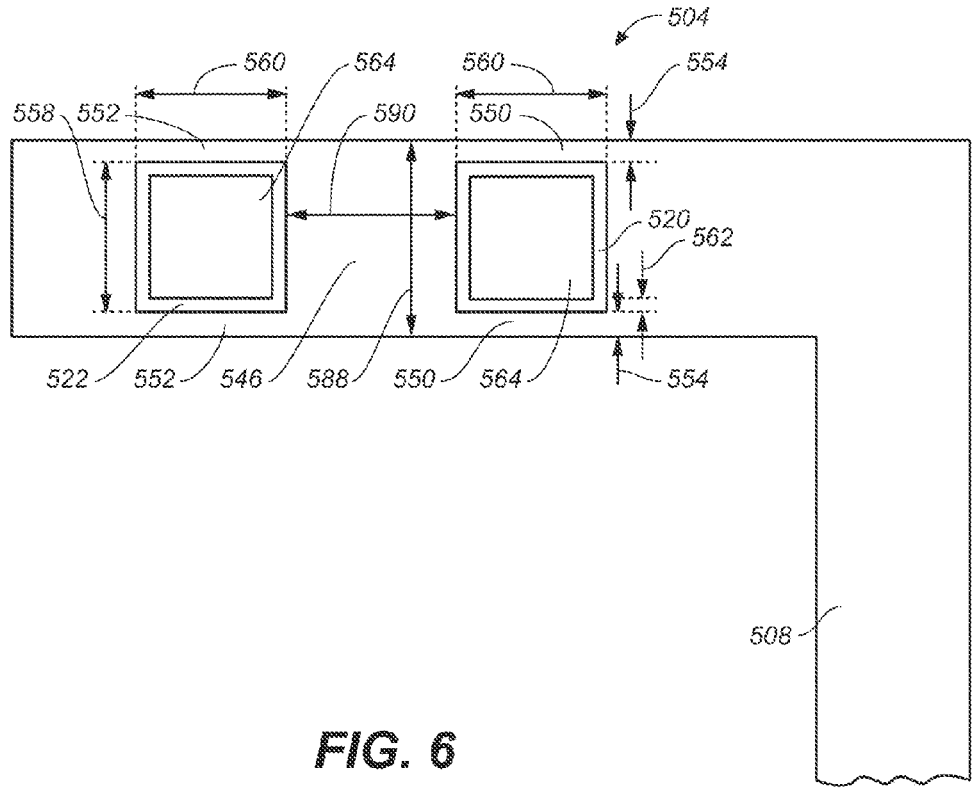
FIG. 6 is an expanded top view of a second zone of the conductive layer as illustrated in FIG. 5.

FIGS. 5 and 6 show that second zone 504 includes a first working pad 514, a first working electrode track 508, two whisker tracks 550, a first working electrode 546, two whisker electrodes 552, a first polygon 520, and a second polygon 522. First working pad 514 is located at proximal portion 578 and is adapted to connect to the test meter. There is an electrically continuous pathway that runs through the following elements which are first working pad 514, first working electrode track 508, the two whisker tracks 550, first working electrode 546, and the two whisker electrodes 552. The two whisker tracks 550 each form an electrically continuous pathway, in parallel, between first working electrode 546 and first working electrode track 508. It is an advantage of this invention in that by having the two whisker tracks 550, electrical continuity can be maintained if a scratch or other insulating damage occurs at one of the two whisker tracks 550.

FIG. 5 shows that optional third zone 506 which includes a second working pad 516, a second working electrode track 510, two whisker tracks 584, a second working electrode 548, two whisker electrodes 586, a first polygon 524, and a second polygon 526. Second working pad 516 is located at proximal portion 578 and is adapted to connect to the test meter. There is an electrically continuous pathway that runs through the following elements which are second working pad 516, second working electrode track 510, the two whisker tracks 584, second working electrode 548, and the two whisker electrodes 586. The two whisker tracks 584 each form an electrically continuous pathway, in parallel, between second working electrode 548 and second working electrode track 510. It is an advantage of this invention in that by having the two whisker tracks 584, electrical continuity can be maintained if a scratch or other insulating damage occurs at one of the two whisker tracks 584.

First polygon 520 and second polygon 522 may both be rectangles, which are equally sized, having a polygon length 560 and a polygon width 558, as illustrated in FIG. 6. An insulatively etched line may be used to form a peripheral boundary portion for first polygon 520 and for second polygon 522. The insulatively etched line may have a line width 562, as illustrated in FIG. 6. First polygon 520 and second polygon 522 may both include a conductive island 564, which is electrically isolated by the insulatively etched line pattern. Line width 562 may have a minimum value of about 1 micron and a maximum value equal to about polygon width 558. It is an advantage of this invention in that the laser ablation process may use less energy when first polygon 520 and second polygon 522 have a laser ablated peripheral boundary in the form of a line, rather than laser ablating both conductive islands 564.

The purpose of first polygon 520 and second polygon 522 is to substantially define the area of first working electrode 546 without using an insulation layer or adhesive layer. Note that insulation layer 16 may be deposed on conductive layer 50 for defining the area of first working electrode 12, as illustrated in FIG. 8. In general, a screen-printed insulation layer does not define the electrode area as well as a laser-etched pattern. As previously mentioned, the edge definition is generally much better for laser ablated patterns as opposed to the granularized edge definition resulting from screen printing.

First working electrode 546 may be in the form of a rectangle having a first working electrode length 590 and a first working electrode width 588, as illustrated in FIG. 6. First working electrode length 590 may be the same as the shortest distance between first polygon 520 and second polygon 522. First working electrode width 588 may be defined by the laser ablated pattern used to define second zone 504 as illustrated in FIGS. 5 and 6.

Polygon width 558 of first polygon 520 must be smaller than first working electrode width 588 so that first polygon 520 may define the two whisker tracks 550, as illustrated in FIG. 6. The two whisker tracks 550 may be in the form of rectangles, each having a whisker width 554 and a whisker length. The distance of the whisker length corresponds to the distance of polygon length 560. The two whisker tracks 550 are located on opposite sides of first polygon 520 and separated by a distance equal to polygon width 558. The sum of the two whisker widths 554 is equal to the difference between first working electrode width 588 minus polygon width 558.

Similarly, polygon width 558 of second polygon 522 must be smaller than first working electrode width 588 so that second polygon 522 may define the two whisker electrodes 552, as illustrated in FIG. 6. The two whisker electrodes 552 may be in the form of rectangles, each having a whisker width 554 and a whisker length. The distance of the whisker length corresponds to the distance of polygon length 560. The two whisker electrodes 552 may be located on opposite sides of second polygon 522 and separated by a distance equal to polygon width 558. The sum of the two whisker widths 554 of whisker electrodes 552 is equal to the difference between first working electrode width 588 minus polygon width 558. Note that whisker tracks 550 differ from whisker electrodes 552 in that whisker tracks provide redundant electrical contacts to working electrode 546.

In an embodiment of this invention, polygon width 558 of first polygon 520 and second polygon 522 may be sufficiently large to form two opposing whisker tracks 550 having a whisker width 554 of about 1 micron to about 20 microns. The lower limit of the range for whisker width 554 is limited by the ability of the laser to accurately register with an edge of second zone 508 and the resulting increased resistance of whisker tracks 550 when whisker width 554 decreases. When the resistance of whisker width 554 becomes sufficiently large, an uncompensated voltage drop develops between the working electrode and the reference electrode causing a decrease in the glucose current. The upper limit of the range for whisker width 554 is selected so that the two whisker tracks 550 contribute to less than about 5% of the total electroactive area of first working electrode 546.

In general, first polygon 520 and second polygon 522 substantially define the electroactive area of first working electrode 546 and partially define the electroactive area of whisker tracks 550 and whisker electrodes 552. As will be later described, adhesive layer 572 in conjunction with first polygon 520 or second polygon 522 will be used to define the area of whisker tracks 550 and whisker electrodes 552. In a similar manner, first polygon 524 and second polygon 526 will substantially define the electroactive area of second working electrode 548 and partially define the electroactive area of whisker tracks 584 and whisker electrodes 586. In a yet similar manner, first polygon 528 and second polygon 530 will substantially define the electroactive area of reference electrode 544 and partially define the electroactive area of whisker tracks 580 and whisker electrodes 582.

Figure 4A:
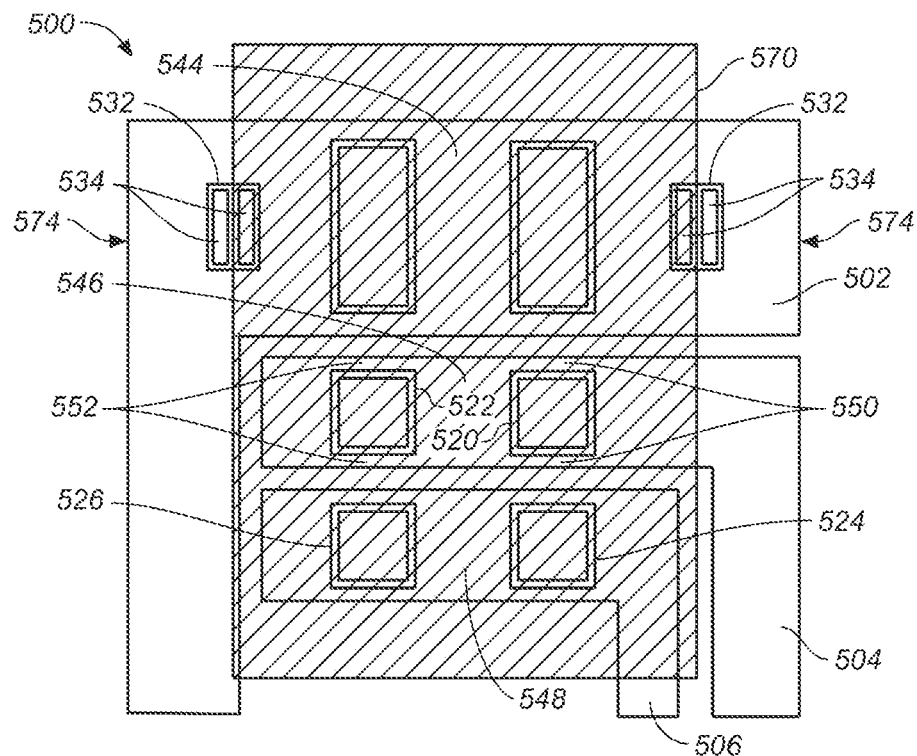
FIG. 4A is a simplified top view of a reagent layer disposed on the conductive layer as illustrated in FIG. 5.

FIG. 4A shows a simplified top view of a reagent layer 570 disposed on a portion of first zone 502, second zone 504, and third zone 506. First zone 502 further includes primary registration marks 532 and secondary registration marks 534 for guiding and/or verifying the alignment of reagent layer 570 onto conductive layer 501. Primary registration marks 532 may be in the form of two rectangles that are near two sides 574 and located on opposite sides of reference electrode 544. Reagent layer 570 may be in the form of a rectangle having two opposing sides, which intersect with primary registration marks 532 for guiding and/or verifying proper alignment. Within an internal portion of primary registration mark 532, there are two secondary registration marks 534 which are also used for guiding and/or verifying proper alignment of reagent layer, in a manner which is more precise than primary registration marks 532. When properly aligned, reagent layer 570 has two opposing sides, which intersect in between the two secondary registration marks 534. Reagent layer 570 may be sized to be sufficiently large to cover at least first working electrode 546, two whisker electrodes 552, two whisker tracks 550, first polygon 520, and second polygon 522. Reagent layer 570 can be deposited on the strip via a BioDot non-contact, drop-on-demand technique.

Under certain circumstances, a reagent layer may be more non-uniform at a peripheral boundary portion. For example, the peripheral boundary portion of a reagent layer may form a raised structure where the reagent layer height at the periphery is much higher than at the center, where the reagent layer height may be more uniform. Therefore, using a reagent layer 570 that is much larger than first working electrode 546 may result in a more uniform portion, which covers first working electrode 546.

Figure 4B:
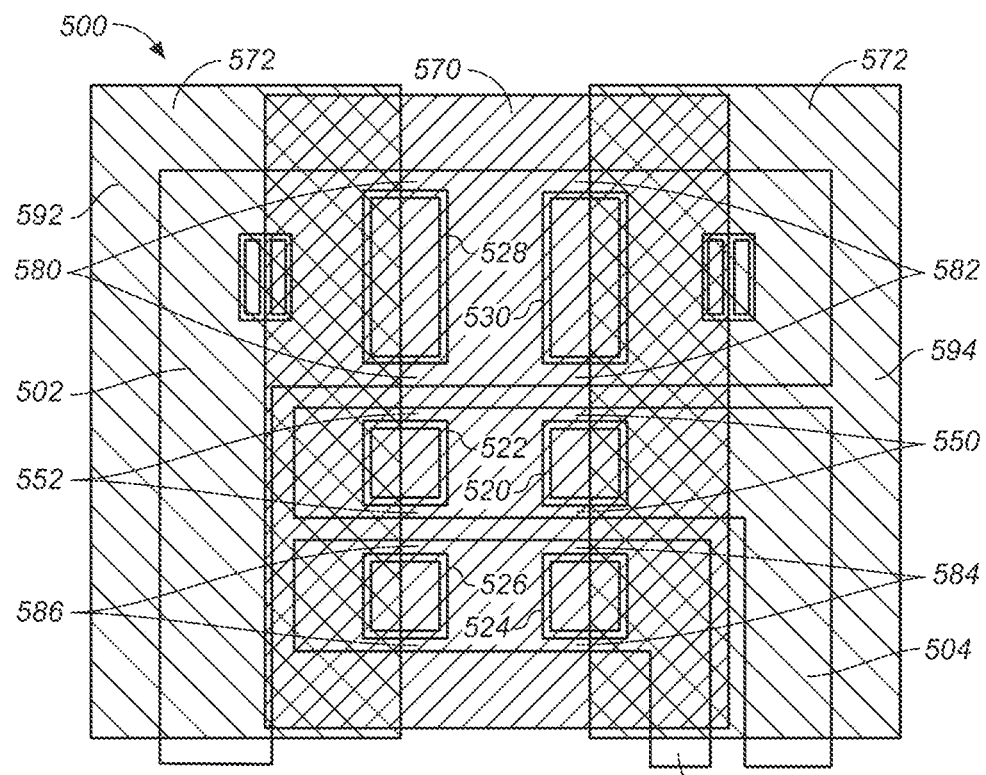
FIG. 4B is a simplified top view of an adhesive layer disposed on the conductive layer and the reagent layer in a manner consistent with FIG. 4A.
Figure 4C:
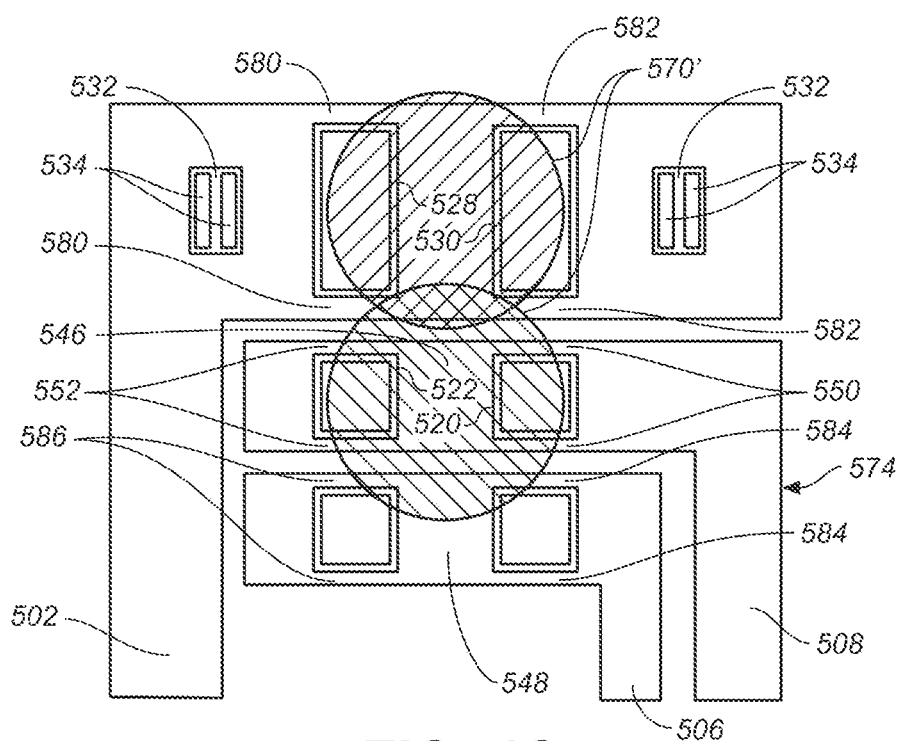
FIG. 4C illustrates a simplified view of a reagent layer on the conductive layer of FIG. 5.

FIG. 4B is a simplified top view of an adhesive layer 572 disposed on a portion of reagent layer 570, first zone 502, second zone 504, and third zone 506. Adhesive layer 572 may include three adhesive spacer pads. Note, however, that for purposes of simplicity, FIG. 4B only shows two of the three adhesive spacer pads, which in this case are adhesive pads (592 and 594). FIG. 4B shows that one side of an adhesive pad 592 intersects with first polygon 528, whisker tracks 580, second polygon 522, whisker electrodes 552, second polygon 526, and whisker electrodes 586. First polygon 528, second polygon 522, and second polygon 526 may be used as a guide for aligning and/or verifying the position of the one side of adhesive pad 592. In addition, an adhesive pad 594 intersects with second polygon 530, whisker electrodes 582, first polygon 520, whisker tracks 550, first polygon 524, and whisker tracks 584. Second polygon 530, first polygon 520, and first polygon 524 may also be used as a guide for aligning and/or verifying the position of the one side of adhesive pad 594. Adhesive layer 572 may be capable of mixing with reagent layer 570 and/or dissolving reagent layer 570 such that adhesive layer 572 may form a liquid impermeable seal to both conductive layer 501 and the substrate. Adhesive layer 572 may be any suitable adhesive, such as, for example, a double-sided pressure sensitive adhesive, a heat activated adhesive, or a screen-printed pressure sensitive adhesive.

Although adhesive layer 572 does not substantially define the area of first working electrode 546, second working electrode 548, and reference electrode 544, the alignment of adhesive layer 572 does substantially affect the electroactive area of whisker electrodes (582, 552, and 586) and whisker tracks (580, 550, and 584), as illustrated in FIG. 5. The electroactive area of whisker electrodes (582, 552, and 586) and whisker tracks (580, 550, and 584) is defined by whisker width 554 and the portion along whisker length 556 that is not covered by adhesive layer 572. For first working electrode 546, whisker width 554 may be sufficiently small such that the electroactive area ascribed to the whisker electrodes 552 and the whisker tracks 550 is a relatively small proportion compared to the electroactive area ascribed to first working electrode 546. In one embodiment, the area of the two whisker tracks 550 and the two whisker electrodes 552 capable of oxidizing a reduced mediator may be about 10% or less than an area of first working electrode 546 capable of oxidizing the reduced mediator. It should be noted that the effective electroactive area of second zone 504 includes first working electrode 546, and the portions of whisker tracks 550 and whisker electrodes 552 not covered by adhesive layer 572. When the total electroactive area of whisker tracks 550 and whisker electrodes 552 are relatively small compared to the working electrode area, the variations in aligning adhesive pads (592 and 594) do not cause a significant variation in the effective electroactive area.

Under certain circumstances, adhesive pads (592 and 594) may be disposed in such a way that a distance between them is constant. In one example, the distance between adhesive pads would be constant if both adhesive pads (592 and 594) were screen printed at the same time using the same screen. In another example, the distance between adhesive pads would be constant if the pads were created from a die cut adhesive roll. Any variations in alignment will cause both adhesive pads (592 and 594) to be skewed closer to one of the sides 574. In one scenario, both adhesive pads (592 and 594) can be skewed such that the electroactive area exposed by adhesive pads (592 and 594) for whisker tracks 550 is larger which in turn causes the electroactive area of whisker electrodes 552 to be proportionally smaller. Similarly, both adhesive pads (592 and 594) can be skewed such that the electroactive area of whisker tracks 550 is smaller which in turn causes the electroactive area of whisker electrodes 552 to be proportionally larger. Because, the distance between both adhesive pads (592 and 594) may be constant, the effective electroactive area of second conductive zone 504 does not vary with the alignment of both adhesive pads (592 and 594). In summary, the use of whisker tracks 550 and whisker electrodes 552 causes the effective electroactive area of second conductive zone 504 to be a precise and constant value even if there is some variation in aligning adhesive pads (592 and 594).

Although the present invention is particularly adapted to the measurement of a glucose concentration in blood, it will be apparent to those skilled in the art that the test strip described herein may be adapted to enable an improved precision for the electrochemical measurement of other analytes. Examples of other analytes that may be measured with the test strip embodiment of the present invention are lactate, ethanol, cholesterol, amino acids, choline, hemoglobin, and fructosamine in blood.

EXAMPLE

The reagent layer was formulated as an enzyme ink suitable for screen printing as follows. 100 ml of 200 mM aqueous phosphate buffer was adjusted to pH 7. A mixture was formed by adding 5 g of hydroxyethyl cellulose (HEC), 1 g of poly(vinyl pyrrolidone vinyl acetate) (PVP-VA S-630), 0.5 ml of DC 1500 Dow Corning antifoam to 100 mL of phosphate buffer and mixed by homogenization. The mixture was allowed to stand overnight to allow air bubbles to disperse and then used as a stock solution for the formulation of the enzyme ink. Next, 7.5 grams of Cab-o-Sil TS610 was gradually added by hand to the mixture until about ⅘ of the total amount of Cab-o-Sil TS610 had been added. The remainder Cab-o-Sil TS610 was added with mixing by homogenization. The mixture was then rolled for 12 hours. About 18 g of ruthenium hexamine ($[Ru^{III}(NH_3)_6]Cl_3$) was then added and mixed by homogenization until dissolved. Finally, 2.8 g of glucose oxidase enzyme preparation (250 Units/mg) was added and then thoroughly mixed into the solution. The resulting formulation was ready for printing, or could be stored with refrigeration. Preferably, the reagent can be made with a mixture of about 10 milliter 0.2 M Potassium Phosphate Buffer at pH 7.0 (0.2 M Monobasic Potassium Phosphate ($KH_2PO_4$) to 0.2 M Dibasic Potassium Phosphate ($K_2HPO_4$) in AnalaR water), about 1 gram of Natrosol 250-L, Hydroxyethyl Cellulose (HEC of means molecular weight of 90 kD) of about 1% of weight over volume, about 1 gram of Ruthenium (III) Hexaamine Trichloride, and about 0.2 gram of Glucose Oxidase. Alternative examples of reagent formulations or inks suitable for use with the embodiments herein can be found in U.S. Pat. Nos. 5,708,247 6,046,051, and 6,241,862; U.S. Pre-Grant Publication No. 20030217918A1; published international applications WO01/67099 and WO01/73124.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods within the scope of these claims and their equivalents be covered thereby.

What is claimed is:
1. An analyte test strip comprising:
   a generally planar substrate that extends from a first end to a second end;
   a first electrode track that extends between the first and second end of the substrate; and
   a first electrode located proximate the first end of the generally planar substrate, the first electrode including:
      a first electroactive area disposed on the substrate proximate the first end, the first electroactive area comprising a single continuous surface area of conductive material and a reagent disposed thereon;
      two spaced-apart first whisker tracks contiguous to both the first electroactive area and one end of the first electrode track;
   a second electrode located proximate the first electrode, the second electrode including:
      a second electrode track that extends between the first and second end of the substrate; and
      a second electrode located proximate the first end, the second electrode including:
         a second electroactive area disposed on the substrate proximate the first electroactive area, the second electroactive area comprising:
            a single continuous surface area of conductive material and the reagent disposed thereon; and
            two spaced-apart second whisker tracks contiguous to both the second electroactive area and the second electrode track;
   a third electrode track that extends between the first and second ends; and a third electrode located proximate the first end, the third electrode including:
  a third electroactive area disposed on the substrate proximate the first and second electroactive areas, the third electroactive area comprising a single continuous surface area of conductive material and the reagent disposed thereon; and
  two spaced-apart third whisker tracks of conductive material contiguous to both the third electroactive area and the third electrode track;
wherein uncovered reagent is disposed over each of the two spaced apart first, second, and third whisker tracks to define respective fourth, fifth, and sixth electroactive areas, and in which each of the fourth, fifth, and sixth electroactive areas is about 10% or less with respect to the first, second and third electroactive areas; and
wherein one of the first, second and third electrodes comprises a generally rectangular shaped electrode having two spaced-apart islands of conductive material located in the electrode and electrically isolated from each of the electrodes, each of the two isolated islands being generally rectangular in shape with at least one side contiguous to one of the two spaced-apart first, second, or third whisker tracks.

2. The test strip of claim 1, in which one of the other of the first, second, and third electrodes comprises a generally rectangular shaped electrode having two spaced-apart islands of conductive material located in each of the electrodes and electrically isolated from each of the electrodes, each of the two islands being generally square in shape with at least one side of one island contiguous to the whisker track.

3. The test strip of claim 1, in which at least one side of the other island is contiguous to a whisker electrode and each whisker track or whisker electrode comprises a width ranging from about 1 microns to about 20 microns.

4. The test strip of claim 3, in which at least one side of the other island is contiguous to a whisker electrode and each whisker track or whisker electrode comprises a width ranging from about 1 microns to about 20 microns.

* * * * *